United States Patent
Guimberteau et al.

(10) Patent No.: US 11,318,156 B2
(45) Date of Patent: May 3, 2022

(54) SOLID INJECTABLE VETERINARY IMPLANTS COMPRISING MONOCYCLIC LACTONE

(71) Applicant: CEVA SANTE ANIMALE, Libourne (FR)

(72) Inventors: Florence Guimberteau, Montussan (FR); Patrick Forget, Merignac (FR)

(73) Assignee: CEVA SANTE ANIMALE, Libourne (FR)

( * ) Notice: Subject to any disclaimer, the term of this patent is extended or adjusted under 35 U.S.C. 154(b) by 0 days.

(21) Appl. No.: 16/604,771

(22) PCT Filed: Apr. 12, 2018

(86) PCT No.: PCT/EP2018/059429
§ 371 (c)(1),
(2) Date: Oct. 11, 2019

(87) PCT Pub. No.: WO2018/189314
PCT Pub. Date: Oct. 18, 2018

(65) Prior Publication Data
US 2020/0222440 A1    Jul. 16, 2020

(30) Foreign Application Priority Data

Apr. 13, 2017 (EP) .................... 17166456

(51) Int. Cl.
*A61K 31/7048* (2006.01)
*A61K 9/00* (2006.01)
*A61K 47/34* (2017.01)

(52) U.S. Cl.
CPC ........ *A61K 31/7048* (2013.01); *A61K 9/0024* (2013.01); *A61K 47/34* (2013.01)

(58) Field of Classification Search
CPC .. A61K 31/7048; A61K 9/0024; A61K 47/34; A61K 33/10; A61K 47/36
See application file for complete search history.

(56) References Cited

U.S. PATENT DOCUMENTS

2013/0143956 A1* 6/2013 Cady .................... A61K 31/365
514/450

FOREIGN PATENT DOCUMENTS

| WO | 01/37811 A1 | 5/2001 |
| WO | 2006/063794 A1 | 6/2006 |
| WO | 2012/013791 A1 | 2/2012 |

OTHER PUBLICATIONS

Camargo et al, Drug Development and Industrial Pharmacy, 39(1); 146-155 (Year: 2013).*
Shih et al: "In vivo and in vitro release of ivermectin from poly(orthoester) matrices. I. Crosslinked matrix prepared from ketene acetal end-capped prepolymer", Journal of Controlled Release, 1993, vol. 25, No. 1-2, pp. 155-162.
Camargo et al: "Ivermectin-loaded microparticles for parenteral sustained release: in vitro characterization and effect of some formulation variables", Journal of Microencapsulation, 2010, vol. 27, No. 7, pp. 609-617.
International Search Report and Written Opinion in corresponding PCT Application No. PCT/EP2018/059429, dated Jul. 16, 2018.
Camargo et al., "Injectable PLA-based in situ forming implants for controlled release of Ivermectin a BCS Class II drug: solvent selection based on physico-chemical characterization." Drug Development and Industrial Pharmacy, 2013, vol. 39, No. 1, pp. 146-155.

* cited by examiner

*Primary Examiner* — Carlos A Azpuru
(74) *Attorney, Agent, or Firm* — Leason Ellis LLP

(57) ABSTRACT

The present invention relates to an injectable implant comprising an effective amount of a macrocyclic lactone, or a salt thereof, and a bioresorbable polymer, and its use in preventing and/or treating parasites infestations in non human mammals, especially pets.

8 Claims, No Drawings

SOLID INJECTABLE VETERINARY IMPLANTS COMPRISING MONOCYCLIC LACTONE

FIELD OF THE INVENTION

The invention relates to a solid injectable implant comprising an effective amount of a macrocyclic lactone, or a salt thereof, and a bioresorbable polymer, and its use in preventing and/or treating parasites infestations in a non human mammal, especially pets, wherein the parasite is *Dirofilaria immitis*.

It is also related to a kit useful in preventing and/or treating parasites in a non human mammal comprising a syringe and 1 to 6 subunits of the solid implant.

Finally, the invention deals with a method of treatment and/or prevention of parasites infestations in a non human mammal, comprising administering to said non-human mammal an effective amount of a macrocyclic lactone, or a salt thereof, in association with a bioresorbable polymer.

BACKGROUND OF THE INVENTION

Non human mammals for example companion animals such as dogs and cats, are often subject to parasites infestations and/or infections. These parasites may be ectoparasites, such as ticks, fleas, scabies, louses/nits, parasitic flies, mosquitoes . . . and endoparasites such as flatworms (or plathelminths), hookworms or roundworms (or nematodes).

More particularly, heartworm is a parasitic roundworm (especially *Dirofilaria immitis*) that spreads from host to host through bites of mosquitoes (intermediate host). The definitive and most affected hosts are dogs but it can also infect cats, wolves, coyotes, foxes, ferrets, sea lions and even bovines and humans. It is most often found in Africa, America, Oceania, Europe and Asia.

The parasite is commonly called "heartworm" because the adult reproductive stage of its life cycle resides primarily in the right ventricle of its host where it can live for many years. Heartworms infection may result in serious diseases for the host: dirofilariasis, and more precisely, heartworm disease.

When a mosquito bites an infected animal, young heartworms, called microfilariae, enter the mosquito's system. Within two weeks, the microfilariae develop into infective larvae inside the mosquito and these infective larvae can be transmitted to other animals when mosquito bites again.

When entering the dog's blood system via this bite, larvae develop (macrofilariae) and migrate to the dog's heart where they mature and breed. The *Dirofilaria* life cycle is completed when the ingested microfilariae mature into infective larvae in the mosquito. Development of larvae into adult worms takes about 180 days in dogs, while, the life cycle of heartworms is approximately 6 months.

*Dirofilaria immitis* appears as white threadlike round worms reaching up to 20 cm long for adult males (12-20 cm) and 31 cm for adult females (25-31 cm), with a mean diameter of 1 mm.

Heartworms are primarily found in the pulmonary artery in dogs with low parasitic burden (<50 worms). In infestations with high parasitic burden (>50 worms), worms may reach the right ventricle, right atrium, and occasionally vena cava. The initial response includes swelling of small pulmonary arteries and blood clotting. The physical presence of heartworms in the pulmonary artery and right ventricle of the canine heart, and the resulting destruction of tissue, causes respiratory and circulatory problems which can be fatal under conditions of stress or vigorous exercise. Pulmonary hypertension and right-sided heart failure may result in congestive heart failure.

Because it is necessary to have a lot of heartworms to clog up blood flow to a significant degree, heartworms can be present inside the heart for up to 2 or 3 years before causing clinical signs. As the disease progresses, lung tissue can be destroyed leading to a worsening cough while liver and kidney damages can occur due to reduced blood flow in organs. If left untreated, heartworm disease may result in death.

Even though safe, highly effective and convenient prevention strategies have been available for the past two decades, heartworm disease, due to *Dirofilaria immitis*, continues to cause severe damages and even death in dogs and other animals (cats, bovines, humans, guinea porcine, and ferrets) in many parts of the world. Moreover, the parasite and vector mosquitoes continue to spread into areas where they have not been reported previously.

The control of such parasites has long been recognized as an important aspect of human and animal health regimens. Although a number of alternatives to control infestations are in use, they suffer from many problems, including a limited spectrum of activity, the need for repeated treatment (lack of compliance) and, in some rare instances, resistance by parasites.

Another roundworm which can be cited is *Dirofilaria repens*. It is most often found in Eastern Europe, Africa and Asia. The worm affects dogs and other carnivores such as cats, wolves, sea lions, foxes, coyotes and muskrats. As with *Dirofilaria immitis* worm, mosquitoes (host and vector) transmit infectious microfilariae, which develop into fertile macrofilariae in their definitive host: the dog. Larvae develop into infective larvae within the mosquito over 10-16 days, before being reintroduced back into a new host. The adults of *Dirofilaria repens* are located in the subcutaneous tissues of dogs and cats, where they mature in 6-7 months. *Dirofilaria repens* appears as white threadlike round worms reaching up to 25 cm long for adult females (25-30 cm) whereas adult males are shorter, with a mean diameter of 1-2 mm.

In both cases (*Dirofilaria repens* and *Dirofilaria immitis*), humans may also become infected as aberrant hosts. But, most infective larvae introduced in human die.

Currently for curative treatment, only two arsenic derivatives are available for clinically infested dogs, namely thiacetarsamide (Caparsolate®, by Abbott Laboratories) which is an old medication, with severe adverse effects and melarsomine dihydrochloride (Immiticide®, by Merial), which is a more recent drug with fewer side effects. For chemoprophylaxis, two alternatives are possible to prevent heartworm disease in dogs: daily administration of diethylcarbamazine citrate, or monthly administration of macrocyclic lactones.

Number of macrocyclic lactones have been commercialized as preventive treatment, for example ivermectin under the name of Ivomec® or Heartgard® (by Merial), doramectin (Dectomax®, by Zoetis), moxidectin and abamectin (Avomec®, by Merial).

Moreover, a slow release formulation of subcutaneously injected moxidectin-impregnated lipid microspheres, providing continuous protection of six months following a single a single dose administration, has been marketed by Zoetis under the name of Moxidectin SR®, ProHeart 6® or Guardian SR® (U.S. Pat. No. 6,340,671). It is a suspension which requires a complex preparation and use in general veterinary practice. Besides, this product has been voluntarily removed from the US market in September 2004 because of safety related issues, and currently has been allowed once again by FDA under a risk minimization and restricted distribution program.

More particularly, ivermectin has been marketed for treatment of various helminth intestinal parasites including *Dirofilaria immitis* and *Dirofilaria repens* in animals. For example, Heartgard® chewable tablets are administered orally, at monthly intervals, at a recommended minimum amount of 6 µg of ivermectin per kilogram (2.72 µm/lb) of body weight. Heartgard® is available in three dosage strengths for dogs of different weights (68, 136 and 272 µg).

For other species like swine, cattle, sheep, and horses, ivermectin is available in 10 mg/mL and 2.7 mg/mL for injectable form; 0.153 percent and 1.87 percent for paste form; 10 mg/mL for liquid oral form.

WO2007024719 relates to a liquid long acting injectable formulation for fighting ectoparasites and/or endoparasites in a mammal comprising ivermectin and polylactide. The formulation has a therapeutic effect for a period of time consisting of at least about four months.

US2017020848 describes an extended release injectable composition for the treatment or prevention of parasite infections in an animal comprising an antiparasitic effective amount of at least one isoxazoline active agent, polylactide, ivermectin, and a solvent or mixture of solvents.

CN103830170 deals with an ivermectin/poly(lactic-co-glycolic acid) (PLGA) in-vivo gel injection aiming to provide a long-acting injection for preventing and treating livestock parasite infections.

CN102302457 relates to ivermectin sustained-release microspheres of PLGA or polylactic acid (PLA) to kill parasites during 103 days.

U.S. Pat. No. 9,351,987 relates to a method of controlling heartworm disease, the method comprising administering to a dog an non bioresorbable implant comprising ivermectin, which is administered every 6 months to 12 months.

But none of the prior art documents discloses a solid implant with a bioresorbable polymer according to the present invention.

Despite the efficacy of above drugs, a problem of safety remains: high plasma total ivermectin concentrations are considered as risk factor for diseases of nervous system in dogs.

In a 36-day-study in beagle dogs wherein ivermectin was administered orally at 0.5 and 2.0 mg/kg of body weight (bw), the concentrations of ivermectin (B1a) in plasma increased dramatically between day two and day eight, and reached steady-state after about three weeks. A four-fold increase in the dose resulted in an average eight-fold increase in plasma levels. Such high plasma levels have been observed to cause adverse effects in dogs. In beagle dogs, mydriasis was the most sensitive indicator of toxicity. More severe signs include ataxia and tremors. Deaths were preceded by a comatose state. For collie dogs, approximately 30% of them were highly sensitive to ivermectin. In a 14-week-oral-study in beagle dogs (4/sex/group), mydriasis and slight weight loss were observed at 1.0 and 2.0 mg/kg bw. Four dogs in the 2.0 mg/kg bw group developed tremors, ataxia, anorexia and dehydration and were killed prior to the end of the study. The No Observable Effect Level (NOEL) was 0.5 mg/kg bw. It is now reported that collies are the most frequently affected dogs (U.S. Pat. No. 9,351,987).

It is known, in humans and in several animal species, that altered expression or function of p-glycoprotein (or multidrug resistance protein 1) could conceivably allow increase of ivermectin brain concentrations and produce severe neurotoxicity. As a consequence of normal dosing regimen for ivermectin, the treated animals necessarily receive a relatively large quantity of the drug which remains effective for an extended period. This in turn means that shortly after treatment the animal has a very high concentration of ivermectin in its bloodstream, which decreases during the remainder of the period.

Furthermore, the currently marketed ivermectin formulations have certain use precautions. The American Heartworm Society (AHS) recognizes the safety-net (or reachback effect) and adulticidal properties of some macrocyclic lactones, particularly ivermectin. However, heartworm-positive working dogs might be more at risk to develop severe thromboembolism and to die. Worsened radiographic and echocardiographic images suggest such treatment is contraindicated. Furthermore, even in asymptomatic dogs, it should be administered with much caution and with examination by a veterinarian at least once every 4-6 months. Likewise, ivermectin must be used with caution in collies and related shepherd dogs that are more susceptible to its neurotoxic effects than other dog breeds.

SUMMARY OF THE INVENTION

Consequently, in order to: overcome the foregoing problems, increase the effectiveness of macrocyclic lactone, and more specially avermectin, to eradicate dirofilariasis, and provide more predictable performance of this drug, there is a need in the art for a dosage form which affords improved absorption and bioavailability of macrocyclic lactone, more precisely avermectin, and more precisely ivermectin, at a lower maximum plasma concentration.

Therefore, the present invention aims to provide novel formulations which are easier to administer and are able to maintain an effective plasma concentration over a prolonged period of.

Implants according to the present invention have numerous advantages. They are safer, less toxic, more stable, and well accepted by the body (biocompatible): there are no relevant local and general negative clinical signs (biochemistry/biology) due to the injection of the implant.

The implants are more effective, have a long half-life, are well absorbed, well distributed, well metabolized and well eliminated by the body (bioerodible, bioresorbable).

The implants are also ready to use. They are easy to use as veterinary medicines: the user neither needs to prepare any suspension or solution by mixing microparticles with an organic/aqueous solvent or any other excipients or liquids, nor need to measure/calculate and extract the convenient amount (volume) of drug from a syringe, according to the weight of the animal. Consequently, there is no risk of dose error. The dosage regimen is perfectly controlled.

Moreover, in case of allergic problems, thanks to the solid form of the implants, it is possible to remove the implant, and stop the treatment at any time. Indeed, as the implants are not gel but solid, they do not spread in the animal, and the kinetic release profile (amount and release regularity) of the active ingredient can easily be controlled. The amount of active ingredient is sustainably diffused during several months, through the polymer, without being damaged thanks to the "protection layer" of polymer, which increases its efficiency. The predictability of the implant efficacy is increased. The implant has an extended release profile. Thanks to this, the maximum concentration ($C_{max}$) of the implant is decreased and the initial release curve is smooth.

Finally, there is no more need of monthly restrictive administrations, resulting in a better observance of the treatment.

Therefore, the problem solved by the present invention, is to provide an easy injectable sterile solid implant to treat and/or prevent parasites infestations in a non human mammal, which has an efficacy and allows an efficient plasma concentration during 4 to 20 months.

In a first aspect, the aim of the present invention is to provide a solid injectable veterinary implant comprising a macrocyclic lactone, or a salt thereof, and a pharmaceutically acceptable bioresorbable polymer.

A further object of the invention is to provide a solid injectable veterinary implant comprising a macrocyclic lactone, or a salt thereof, and a pharmaceutically acceptable bioresorbable polymer for use in preventing and/or treating parasites infestations in a non human mammal.

A third object of the invention is to provide a kit useful in preventing and/or treating parasites in a non human mammal comprising a syringe and 1 to 6 sub-units of said solid implant.

Moreover, the invention discloses a method of treatment and/or prevention of parasites infestations in a non-human mammal, comprising administering, to said non-human mammal, the said solid injectable veterinary implant.

DETAILED DESCRIPTION OF THE INVENTION

In a first aspect, this invention relates, to a solid injectable veterinary implant comprising a macrocyclic lactone, or a salt thereof, and a pharmaceutically acceptable bioresorbable polymer.

Macrocyclic lactones are classified in two groups of structurally related molecules: milbemycins and avermectins.

Milbemycins are used as antiparasitic agents against worms, ticks and fleas. According to the present application, milbemycins mean milbemycin oxime, moxidectin, or mixtures thereof, and more preferably the milbemycin is the moxidectin.

The moxidectin has the structural formula (milbemycin B, cas no 11350706-5, molecular weight 639.8 g·mol$^{-1}$):

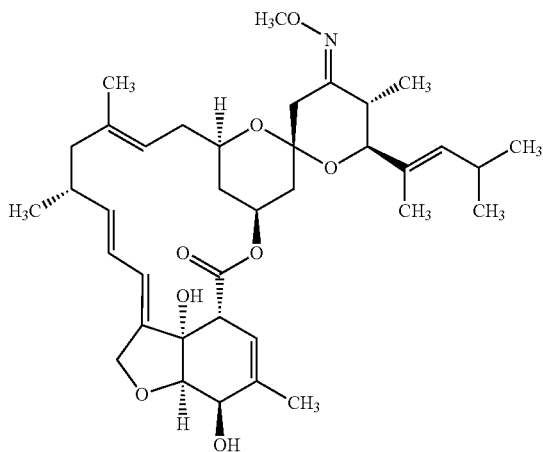 [SMILES: CO/N=C1\C[C@]2(C[C@@H]3C[C@@H](C/C=C(\C)C[C@@H](C)/C=C/C=C4\CO[C@@H]5[C@H](O)C(C)=C[C@@H](C(=O)O3)[C@]45O)O2)O[C@H](/C(C)=C/C(C)C)[C@H]1C]

Avermectins are 16-membered macrocyclic-lactone derivatives used as anthelmintics and insecticides drugs. They block the transmission of electrical activity in invertebrates nerves and muscles cells, causing the paralysis of their neuromuscular system. According to the present application, avermectin means ivermectin, doramectin, abamectin, eprinomectin or selamectin, or mixtures thereof.

Avermectin according to the present invention is preferably ivermectin. Ivermectin consists of a mixture of two structurally similar compounds, 22,23-dihydroavermectin B1a (H2B1a, not less than 80%, cas no 70288-86-7, molecular weight 875.1 g·mol$^{-1}$) and 22,23-dihydroavermectin B1b (H2B1b, not more than 20%, cas no 71827-03-7, molecular weight 861.07 g·mol$^{-1}$) as described in U.S. Pat. No. 4,199, 569.

The structural formulas are:

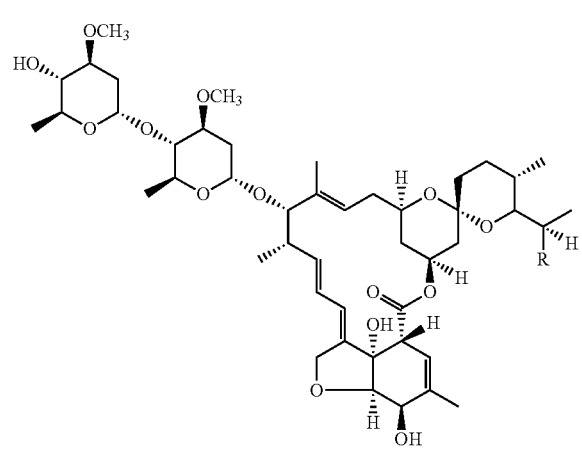

Component H$_2$B$_{1a}$: R=CH$_2$CH$_3$ Component H$_2$B$_{1b}$: R=CH$_3$

Preferred macrocyclic lactones according to the present invention are selected from milbemycin oxime, moxidectin, ivermectin, doramectin, abamectin, eprinomectin, and selamectin or mixtures thereof. Even more preferably, the macrocyclic lactone is ivermectin or a salt thereof.

The terms avermectins and milbemycins also comprise their pharmaceutically acceptable salts. These pharmaceutically acceptable salts include inorganic acid salts as well as organic acid salts. The inorganic acid salt can be hydrochloride, hydrobromide, phosphate, nitrate sulfate, and the like. The organic acid salts include fumarate, citrate, tartrate, acetate, maleate, toluenesulfonate, methanesulfonate and the like.

More particularly, the amount of macrocyclic lactone, or a salt thereof, is comprised between 5 and 60 wt % of the total implant weight, between 10-50 wt %, between 10-40 wt % between 10-30 wt %, between 10-20 wt %, between 10-15 wt %, between 11-15 wt %, between 12-15 wt %, and even more preferably between 13 and 15 wt %, and the preferred macrocyclic lactone is an avermectin, more preferably ivermectin.

The implant according to the present invention comprises a pharmaceutically acceptable bioresorbable polymer.

Within the context of the invention, "bioresorbable" refers to materials that can be broken down, deteriorated, degraded, absorbed, and eliminated, directly by the body and that do not require mechanical or manually removal, such as sutures. These are substrates capable of at least partially resorb upon contact with a target biological tissue in a defined amount of time dependent on the composition.

The terms bioresorbable, bioabsorbable, biocompatible, biodegradable, bioerodible are used interchangeably. They refer to polymers that are capable of being partially and/or completely degraded and/or eroded into different degrees of molecular levels in the body, once their clinical purpose has been served. They are exposed to body fluids such as blood, lymph, juice . . . and are gradually resorbed, absorbed, degrade, erode and/or eliminated by the body. The processes of deterioration and absorption of the polymer can be caused, for example, by hydrolysis, cellular actions, and/or metabolic processes (catabolism, anabolism . . . ). In case of hydrolysis, the rate of hydrolysis depends on many factors such as the size and hydrophilicity of the particular polymer, the degree of crystallinity of the polymer, and the pH and the temperature of the body. In general, degradation will be shorter for polymers with lower molecular weights or greater hydrophilicity.

As an example, when polylactide (a known bioresorbable polymer) is exposed to aqueous media such as buffers or tissue, water is absorbed and reacts with the ester linkages, thus breaking the polymer backbone. One hydroxyl group and one carboxylic acid group forms for each ester linkage is hydrolyzed. Slowly, the reduction in molecular weight leads to a reduction in physical properties and the formation of water-soluble fragments. These fragments diffuse away from the polymer and are ultimately hydrolyzed to lactic acids which are processed to normal metabolic pathways.

The pharmaceutically acceptable polymer can also be biostable which refers to polymers that are not immediately bioresorbable, and are chemically/biologically stable in the body for several months: from 4 to 20 months, for example. Biostable polymers of the present invention have a controllable and/or selectable resorption rate. Consequently, a kinetic release profile/rate (amount of drug released per unit of time as defined by in vitro (not in vivo) testing) of the present application active ingredient can be drawn:
- 15% of macrocyclic lactone dose is released in 0 to 50 hours,
- 30% of macrocyclic lactone dose is released in 20 to 250 hours,
- 50% of macrocyclic lactone dose is released after 25 hours,
- 80% of macrocyclic lactone dose is released after 100 hours.

More preferably this kinetic release applies to avermectin, and more preferably to ivermectin.

The amount of bioresorbable polymer is preferably comprised between 15 and 70 wt % of the total implant weight, between 20-68 wt %, between 25-68 wt %, between 30-68 wt %, between 35-68 wt %, between 40-68 wt %, even more preferably between 40-67 wt % of the total implant weight.

The bioresorbable polymer according to the present invention is preferably selected from the group consisting of polylactides, polyvinylic alcohol, polyglycolides, polycaprolactones, polyorthoesters, polyurethanes, polysaccharides, polyethylene glycol, polyethylene oxide, polyphasphazenes, polyamides, polyiminocarbonates, polyphosphoesters, polyorthoesters, polyanhydrides, polyorthoesters, polyhydroxyvalerates, polyhydroxybutyrates, polyamino acids, copolymers thereof, or mixtures thereof. Polysaccharides include amidon, chitin, chitosan, pectins, lignocellulose, ethylcellulose, alginate, hyaluronic acid, copolymers thereof or mixtures thereof, and the like.

When the crystalline PGA (polyglycolic acid) is copolymerized with PLA to form PLGA, the degree of crystallinity is reduced and, as a result, this leads to increases in rates of hydration and hydrolysis. In general, the higher is the content of glycolide, the quicker is the rate of degradation. As the PLA is degraded/hydrolysed slowly, the PLA amount is reduced compared with an implant of PLGA or other polymers. The viscosity has to be adapted: high viscosity avoids the polymer resorbability and creates an "implant collar" in the animal, year after year, and low viscosity polymer resorbs very fast and decreases the implant efficiency. For example, PLA is resorbable in 12-24 months, acrylic polymers are not resorbable, alginates are resorbable in 3-6 months, PLGA is resorbable in 6 months. For all these reasons (viscosity, low hydrolysis, specific molecular weight, no collar . . . ), the preferred bioresorbable polymer according to the present invention is polylactic acid. More preferably, the polylactic acid has an average molecular mass of 18-28 kDa.

Polylactic acid, poly(lactic acid) or polylactide refers to poly(D,L-lactide) (PDLA) which has no side effects, a glass transition temperature Tg equal to 48-52° C., a viscosity of 0.25-0.35 dL/g, and the below formula:

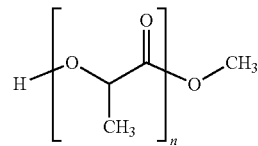

The Resomer R 203H® from Evonik® is preferably used. It is a poly(D,L-lactide) with an acid end group, a viscosity of 0.25-0.35 dL/g, an average molecular mass of 18-28 kDa, which is soluble in acetone, chloroform dimethylformamide, dimethylsulfoxide, dioxane, ethyl acetate, hexafluoroisopropanol and tetrahydrofuran.

The implant according to the present invention refers to a bioactive device, matrix or carrier, such as subcutaneous drug delivery device, in the form of an injectable pill/pellet/capsule/granule/sugar-coated pill/tablet/gelule which have a medical purpose, as for example treat and/or prevent diseases.

In one embodiment of the invention, each implant has a weight between 10 and 30 mg, preferably between 15 and 30 mg, preferably between 15 and 25 mg, preferably between 15 and 20 mg, and more preferably a weight of about 15 mg.

In the entire specification of the present invention, the term about applied to a numerical value means a value of 10% above or below the numerical value.

The implant has preferably a rod-like shape, it is preferably white, and has a breaking force of 25-35N (measured with an hardness tester, as described in USP no 1217). The implant diameter is preferably comprised between 1.5 and 4 mm (+/−0.1 mm) with a preference for a diameter of about 2.3 mm, and has a thickness comprised between 1.5 and 6 mm (+/−0.2 mm), with a preferred thickness of about 3 mm.

"Rod-like shape" may be circular, elliptical, cylindrical, tubular shapes.

The implant according to the invention is solid, semi-solid, a pill, a pellet, a capsule, a granule, a sugar-coated pill, a tablet, a gelule powder and the like.

The implant according to the present invention is solvent free. The final implant comprises less than 5000 ppm of residual organic solvents such as acetone, dimethylsulfoxide (DMSO), ethyl acetate . . . , less than 60 ppm of chloroform, and less than 720 ppm of tetrahydrofuran (THF), or less than 5% of the above listed liquid solvents.

The implant is also an extended release implant. The meaning of "extend release" relates to dosage forms that are formulated in such a manner as to make the contained medicine available over an extended period of time, hence reduction in dosing frequency as compared to conventional dosage form, for example a solution or an immediate release dosage form. Herein, the particular implant formulation with polymer induce extended release characteristics of the drug compared to the active ingredient alone: polymer is responsible for the long acting effect of the implant. The active ingredient is delivered for a prolonged period of time after its administration. The extended release profile depends on, for example, solubility, bioavailability, pH, species . . . .

In a particular embodiment, the implant according to the present invention further comprises one or more additional active substances like ectoparasitic or endoparasitic control agents.

An active substance refers to any substance intended to be used to prepare a medicine, and, when it is used in the manufacture of the medicine, becomes an active substance of this medicine, such substances are intended to supply a pharmacological activity or another direct effect for the diseases diagnosis, healing, attenuation, treatment or prevention or to produce an effect on the body structure and function (as defined in pharmacopeias).

Preferred ectoparasitic agents according to the present invention are selected from: organochlorines, organophosphates, formamidines, amidines, carbamates, pyrethroids, pyrethrins, phenylpyrazoles, benzoylureas, neonicotinoids, oxadiazines, spinosyns, isoxazoline, cholinesterase inhibitors, insect growth regulators, with more precisely permethrin, lindane, sulfur, dicophane, benzyl benzoate, crotamiton and the like.

Preferred endoparasitic agents according to the present invention are selected from: benzimidazoles, imidazothiazoles, tetrahydropyrimidines, isoquinolines, salicylanilides, tetrahydropyrimidines, amino-acetonitrile derivatives, depsipeptides, spiroindoles, with more precisely permethrin, praziquantel, epsiprantel, oxfendazole, fenbendazole, albendazole, levamisole, pyrantel tartrate, triclabendazole, brotianide, clioxanide, closantel, niclosamide, oxyclozanide, rafoxanide and the like.

All these active substances are sparingly/poorly soluble (1 g of active substance for 100-1000 mL of solvent at 15-25° C.), very poorly soluble (1 g of active substance for 1000-10 000 mL of solvent at 15-25° C.) or almost insoluble (1 g of active substance for more than 10 000 mL of solvent at 15-25° C.) in solvents (as defined in pharmacopeias). They are thus advantageously added to the implant according to the present invention.

In a further embodiment of the invention, the implant further comprises one or more excipients: one or more antioxidants, one or more flowing agents, one or more lubricants, one or more diluents, and/or one or more preservatives.

An excipient, or auxiliary substance, refers to any drug component which is not an active substance (such as adjuvants, stabilizers, diluents, antioxidants, antimicrobial preservatives . . . ), according to pharmacopeias.

Antioxidants may be selected from: 2,6-Di-tert.-butyl-4-methylphenol (butyl hydroxytoluene or BHT), vitamin E (DL-alpha-tocopherol, E307), vitamin E phosphate, vitamin A, polyphenols, butyl hydroxyanisol (BHA), propylgallate, tocopherol, ascorbic acid, citric acid, di-alpha-tocopheryl phosphate, beta-carotene, carotenes, carotenoids, flavonoids, and mixtures thereof . . . . The preferred antioxidant are BHT and vitamin E, and more preferably BHT. Antioxidants are present in an amount of between 0.001 and 2%

Flowing agents may be selected from: anhydrous colloidal silica (CAB-O-SIL®), talc, calcium carbonate, and mixtures thereof . . . . The preferred flowing agent is colloidal silica. Flowing agents are present in an amount of 0.01-2%.

Lubricants may be selected from: oils, waxes, stearic acid, stearates (magnesium stearate: LIGAMED MF-2V®, calcium stearate . . . ), talc, long chain fatty acids, polyethylene glycol, palmitic acid, hydrogenated vegetable oils, sodium stearyl fumarate, sodium benzoate, and mixtures thereof . . . . The preferred lubricant is magnesium stearate. Lubricants are present in an amount of 0.01-2%.

Diluents may be selected from: maltodextrine (Glucidex 19 D®), lactose monohydrate, calcium carbonate, sodium carbonate, calcium phosphate or sodium phosphate, starch, saccharose, microcrystalline cellulose, sorbitol, mannitol, xylitol, and mixtures thereof . . . . The preferred diluent is maltodextrine. Diluents are present in an amount of 15-60%.

Preservatives may be selected from: methyl p-hydroxybenzoate, ethyl p-hydroxybenzoate, phenol, sorbic acid, cresol and chlorocresol, and mixtures thereof . . . . Preservatives are present in an amount of 0.01-5%.

In a further embodiment of the invention, the implant is a ready-to-use implant. Ready-to-use herein refers to implants which are manufactured as pills and are intended to be injected as they are sold: no need of preceding mixing or any other preparation/transformation. It avoids the multi-steps mixing for the user. It eliminates the need to procure ancillary equipments, for example syringe, and it minimizes the potential for medicine preparation errors. The implant does not require any step of reconstitution. The implant is not diluted with any diluents before administration.

All embodiments described above for the solid injectable veterinary implant also apply to the use of said implant, to the method of treatment, and to kits comprising said implant, as described below.

Another object of the present invention is a solid injectable veterinary implant comprising macrocyclic lactone, or a salt thereof, and a pharmaceutically acceptable bioresorbable polymer, for use in preventing and/or treating parasites infestations in a non human mammal.

"Preventing and/or treating" as used herein include the control, the reduction, the progression slowing, the eradication, the cure and/or avoid parasites infestations.

In a particular embodiment, the implant has an efficacy of 4 to 20 months. "Efficacy" used herein refers to a therapeutically effective amount of the active substance (5-60 wt % of a macrocyclic lactone for the total implant weight) to treat and/or prevent diseases. Examples of effective injected amounts, of a 15 mg-implant, in dogs, are:

dogs <15 kg (33 lbs): 1 sub-unit,
dogs 15-30 kg (33-66 lbs): 2 sub-units,
dogs 30-45 kg (66-99 lbs): 3 sub-units,
dogs 45-60 kg (99-132 lbs): 4 sub-units,
dogs 60-75 kg (132-165 lbs): 5 sub-units,
dogs >75 kg (>165 lbs): 6 sub-units.

The implant according to the present invention allows to deliver a macrocyclic lactone plasma concentration in the animal of from 0.025 to 90 ng/mL, from 0.025 to 85 ng/mL, from 0.025 to 80 ng/mL, from 0.025 to 75 ng/mL, from 0.025 to 70 ng/mL, from 0.025 to 65 ng/mL, from 0.025 to 60 ng/mL, from 0.025 to 55 ng/mL, from 0.025 to 50 ng/mL, from 0.025 to 40 ng/mL, from 0.025 to 30 ng/mL, from 0.025 to 20 ng/mL, from 0.025 to 10 ng/mL, from 0.025 to 5 ng/mL, more preferably from 0.025 to 10 ng/mL.

When the implant is used according to the present invention, the effective macrocyclic lactone plasma concentration is maintained for a period of at least 4 months, or at least 5 months, or at least 6 months, or at least 7 months, or at least 8 months, or at least 9 months, or at least 12 months, or at least 15 months, or at least 18 months, or preferably at least 20 months, or more.

In a preferred embodiment, the amount of macrocyclic lactone, specially avermectin, more preferably ivermectin, is sufficient to achieve plasma concentration in the animal above 0.025 ng/mL, for a period of at least 12 months, or of 12 months, or for a period of at least 18 months, or of 18 months. More specially, for a dog of 12-15 kg, the amount of macrocyclic lactone, specially avermectin, more preferably ivermectin, is sufficient to achieve plasma concentration in an animal of 12-15 kg, of from 0.025 to 10 ng/mL, or from 0.025 to 8 ng/mL, for a period of at least 12 months, or of 12 months, or for a period of at least 18 months, or of 18 months.

In a preferred embodiment, the implant is administered preferably every 4 months, preferably every 5 months, preferably every 6 months, preferably every 7 months, preferably every 8 months, preferably every 9 months, preferably every 12 months, preferably every 15 months, more preferably every 18 months, and even more preferably every 20 months.

"Administered" herein means the solid implant is easily injected via parenteral routes, like subcutaneously or intramuscularly routes, thanks to a needle and/or a syringe.

In a particular embodiment, the implant is used in preventing and/or treating dirofilariasis, more particularly heartworm disease. The parasite is the heartworm (*Dirofilaria immitis*), or *Dirofilaria repens*, or other roundworms like hookworms. "Heartworm" refers to roundworms that typically reside within the heart of a host during the final reproductive stage of its life cycle, it includes *Dirofilaria immitis*. Killed parasites are more precisely *Dirofilaria immitis* L3-L4 larvae and microfilariae, larval and adults hookworms (*Ancylostoma caninum* and *Uncinaria stenocephala*).

More precisely, the implant prevents heartworm disease caused by *Dirofilaria immitis*, treats existing larval and adults hookworm infestations and treats *Dirofilaria immitis* circulating microfilariae and L3-L4 larvae in heartworm positive dogs.

"Non-human mammals" refers to any mammals able to develop pathologies related to parasites such as heartworms or hookworms, such as, for example, pets, including cats and dogs, wolves, coyotes, foxes, ferrets, sea lions and bovines. In a preferred embodiment of the invention, the non-human mammal is a pet, such as a canine.

Another object of the present application is a kit useful in preventing and/or treating parasites in a non-human mammal comprising a syringe and 1 to 6 sub-units of 10 mg to 30 mg of solid implant as described above. The implant is contained in a syringe/needle kit. According to different dosages, the kit contains 1 to 6 sub-units of implant. It contains 1 sub-unit, 2 sub-units, 3 sub-units, 4 sub-units, 5 sub-units, or 6 sub-units.

Another object of the present invention is a method of treatment and/or prevention of parasites infestations in a non-human mammal, comprising administering to said non-human mammal a solid injectable veterinary implant comprising macrocyclic lactone, or a salt thereof, and a bioresorbable polymer with the embodiments as described above.

Another object of the application is the manufacturing process of the implant, comprising the following steps:

a) dry blend macrocyclic lactone and a diluent, b) mix the bioresorbable polymer with one or more antioxidants, c) dissolve the mix obtained in b) with a solvent, d) pulverize the composition c) on the mix a), under stirring to form grains, e) dry the grains in a oven at 45° C. to evaporate the solvent, f) calibrate the grains on a 500 µm grid, g) mix the grains f) with a lubricant and a flowing agent, h) compress the grains g) in the form of an implant, i) optionally, dry the implant during 3 hours, at about 60° C. to evaporate the solvent, j) sterilize the implant.

The terms diluent, antioxidant, flowing agent and lubricant refer to the above definitions of excipients.

The used solvents can be DMSO, ethyl acetate, chloroform, THF and the like, or mixtures thereof, the preferred one being acetone.

Three methods can be used to sterilize the implant according to the present invention: e-beam rays, gamma and X-rays, gamma rays in cold conditions, and a gaseous method with ethylene oxide, the preferred ones being the gamma rays method in cold conditions, and ethylene oxide gaseous method, and more preferably ethylene oxide gaseous method.

As ivermectin is heat sensitive, the implant cannot be prepared with an extrusion process, but is prepared by wet-granulation in a high shear granulator and compression, with conventional tableting equipment (column or rotary tableting press) processes. The acetone is eliminated after granulation during the manufacturing process, so it doesn't appear in the final implant composition.

Described herein below are examples: preparation of an injectable implant according to the present invention (see examples 1 and 2). These examples are illustrative and in no way limiting.

EXAMPLES

Example 1: Implant Formulation

Implant Formulation Process 26.2 g of ivermectin and 77.5 g of maltodextrin are dry blended. A solution comprising 70.7 g of polylactide, 0.4 g of vitamin E and 0.2 g of butyl hydroxytoluene (BHT) dissolved in 106.0 g of acetone is pulverized on the dry mixture under stirring to form grains. These grains are then dried in an oven at 45° C. and calibrated on a 500 µm grid. Then, 138.6 g of grains are mixed with 1.1 g of magnesium stearate and 0.4 g of colloidal silica, and then compressed in the form of a 15 mg implant.

Pharmacokinetics Study of the Implant

These implants are subcutaneous administered to 4 beagle dogs of 12.4 kg, 14.1 kg, 14.9 kg and 13.2 kg. Ivermectin plasmatic profiles (ng/mL) are measured during 280 days (see results in table 1).

TABLE 1

| | dog weight | | | |
| --- | --- | --- | --- | --- |
| day | 12.4 kg | 14.1 kg | 14.9 kg | 13.2 kg |
| 0 | 0 | 0 | 0 | 0 |
| 30 | 1.016 | 0.443 | 0.311 | 0.218 |
| 80 | 0.210 | 0.309 | 0.404 | 0.183 |
| 100 | 0.196 | 0.312 | 0.247 | 0.220 |
| 140 | 0.259 | 0.470 | 0.144 | 0.182 |
| 160 | 0.425 | 0.449 | 0.139 | 0.284 |
| 180 | 0.391 | 0.377 | 0.162 | 0.264 |
| 200 | 0.476 | 0.332 | 0.145 | 0.271 |

TABLE 1-continued

|  | dog weight | | | |
| --- | --- | --- | --- | --- |
| day | 12.4 kg | 14.1 kg | 14.9 kg | 13.2 kg |
| 220 | 0.758 | 0.322 | 0.138 | 0.247 |
| 240 | 0.885 | 0.427 | 0.121 | 0.288 |
| 260 | 0.898 | 0.234 | 0.105 | 0.331 |
| 280 | 0.578 | 0.097 | 0.094 | 0.28 |

It can be concluded that the plasmatic concentration stays at an efficient level: i.e up to 0.1 ng/mL, during more than 280 days.

Example 2: Implant Formulation

The same process as for example 1 is used. An additional step of drying the implant during 3 hours, at 60° C., is realized to guarantee an acetone amount lower than 0.5%.

TABLE 2

|  | mg/implant |
| --- | --- |
| ivermectin | 2 |
| polylactide | 10 |
| BHT | 0.02 |
| vitamin E | 0.03 |
| colloidal silica | 0.038 |
| magnesium stearate | 0.113 |
| maltodextrin | 2.799 |
| Total weight | 15 |

Example 3: Implant Formulation

The same process as for example 1 is used.

TABLE 3

|  | mg/implant |
| --- | --- |
| ivermectin | 2 |
| polylactide | 6 |
| BHT | 0.02 |
| vitamin E | 0.03 |
| colloidal silica | 0.038 |
| magnesium stearate | 0.113 |
| maltodextrin | 6.8 |
| Total weight | 15 |

Example 4: Implant Formulation

Implant Formulation Process 43.4 of ivermectin and 36.6 g of lactose monohydrate are dry mixed. A solution comprising 20 g of polylactide in 46.7 g of acetone is pulverized on the dry mixture under stirring to form grains. These grains are then calibrated on a 1000 μm grid and 500 μm grid. Then, 79.2 g of grains are dried and mixed with 0.8 g of magnesium stearate and then compressed in the form of a 15 mg implant.

Pharmacokinetics Study of the Implant

These implants are subcutaneous administered to 3 beagle dogs of 14.24 kg, 13.8 kg and 13.1 kg. Ivermectin plasmatic profiles (ng/mL) are measured during 555 days (see results in table 4).

TABLE 4

|  | dog weight | | |
| --- | --- | --- | --- |
| day | 14.2 kg | 13.8 kg | 13.1 kg |
| 0 | 0 | 0 | 0 |
| 30 | 1.633 | 0.677 | 1.088 |
| 80 | 0.761 | 0.467 | 0.445 |
| 100 | 1.23 | 0.528 | 0.792 |
| 140 | 0.734 | 0.458 | 1.019 |
| 160 | 0.835 | 0.652 | 1.171 |
| 180 | 0.922 | 0.601 | 1.451 |
| 200 | 0.825 | 0.751 | 1.047 |
| 220 | 0.653 | 0.726 | 1.125 |
| 240 | 0.565 | 0.673 | 0.708 |
| 270 | 0.516 | 0.83 | 0.766 |
| 300 | 0.538 | 0.715 | 0.583 |
| 330 | 0.771 | 1.309 | 0.747 |
| 360 | 0.614 | 0.838 | 1.107 |
| 390 | 0.69 | 0.564 | 2.362 |
| 420 | 0.302 | 0.915 | 0.649 |
| 450 | 0.149 | 0.626 | 0.369 |
| 480 | 0.119 | 0.617 | 0.265 |
| 510 | 0.092 | 0.27 | 0.233 |
| 525 | 0.094 | 0.185 | 0.195 |
| 540 | 0.096 | 0.12 | 0.17 |
| 555 | 0.102 | 0.1 | 0.101 |

It can be concluded that the plasmatic concentration stays at an efficient level: i.e up to 0.1 ng/mL, during more than 555 days.

The invention claimed is:

1. A solid injectable veterinary implant comprising a macrocyclic lactone or a salt thereof, and a pharmaceutically acceptable bioresorbable polymer, wherein the macrocyclic lactone is ivermectin and the pharmaceutically acceptable bioresorbable polymer is polylactic acid, and wherein the implant is ready to use.

2. The implant according to claim 1, wherein the amount of ivermectin or a salt thereof, is between 5 and 60 wt % of the total implant weight.

3. A solid injectable veterinary implant, comprising (i) ivermectin or a salt thereof, and (ii) polylactic acid, wherein the amount of polylactic acid is between 15 and 70 wt % of the total implant weight.

4. A solid injectable veterinary implant, comprising (i) ivermectin or a salt thereof, and (ii) polylactic acid, wherein the polylactic acid has a molecular mass of 18-28 kDa.

5. The implant according to claim 1, wherein said implant has a weight between 10 and 30 mg.

6. The implant according to claim 1, wherein the implant is solvent free.

7. The implant according to claim 1, wherein the implant further comprises one or more antioxidants, one or more flowing agents, one or more lubricants, one or more diluents, and/or one or more preservatives.

8. A kit useful in preventing and/or treating parasites in a non-human mammal comprising a syringe, and 1 to 6 sub-units of 10 mg to 30 mg of the implant of claim 1.

* * * * *